US00PP32622P2

(12) United States Plant Patent
Lannes

(10) Patent No.: US PP32,622 P2
(45) Date of Patent: Dec. 15, 2020

(54) ***MANDEVILLA* PLANT NAMED 'LANCONNECTICUT'**

(50) Latin Name: *Mandevilla sanderi*
Varietal Denomination: Lanconnecticut

(71) Applicant: Robert Lannes, Malause (FR)

(72) Inventor: Robert Lannes, Malause (FR)

(73) Assignee: D.H.M. Innovtion S.A.S., Malause (FR)

( * ) Notice: Subject to any disclaimer, the term of this patent is extended or adjusted under 35 U.S.C. 154(b) by 0 days.

(21) Appl. No.: 16/873,006

(22) Filed: Jan. 14, 2020

(51) Int. Cl.
*A01H 6/08* (2018.01)
*A01H 5/02* (2018.01)

(52) U.S. Cl.
USPC ..... Plt./232

(58) Field of Classification Search
USPC ..... Plt./232
CPC ..... A01H 6/08; A01H 5/02
See application file for complete search history.

(56) References Cited

PUBLICATIONS

PLUTO Plant Variety Database Jul. 4, 2020.*

* cited by examiner

*Primary Examiner* — Annette H Para
(74) *Attorney, Agent, or Firm* — C. A. Whealy

(57) ABSTRACT

A new and distinct cultivar of *Mandevilla* plant named 'Lanconnecticut', characterized by its broadly upright to trailing plant habit; moderately vigorous growth habit; freely branching habit; glossy dark green-colored leaves; early and freely flowering habit; and bright yellow-colored flowers with yellow orange-colored throats.

2 Drawing Sheets

Figure 1:
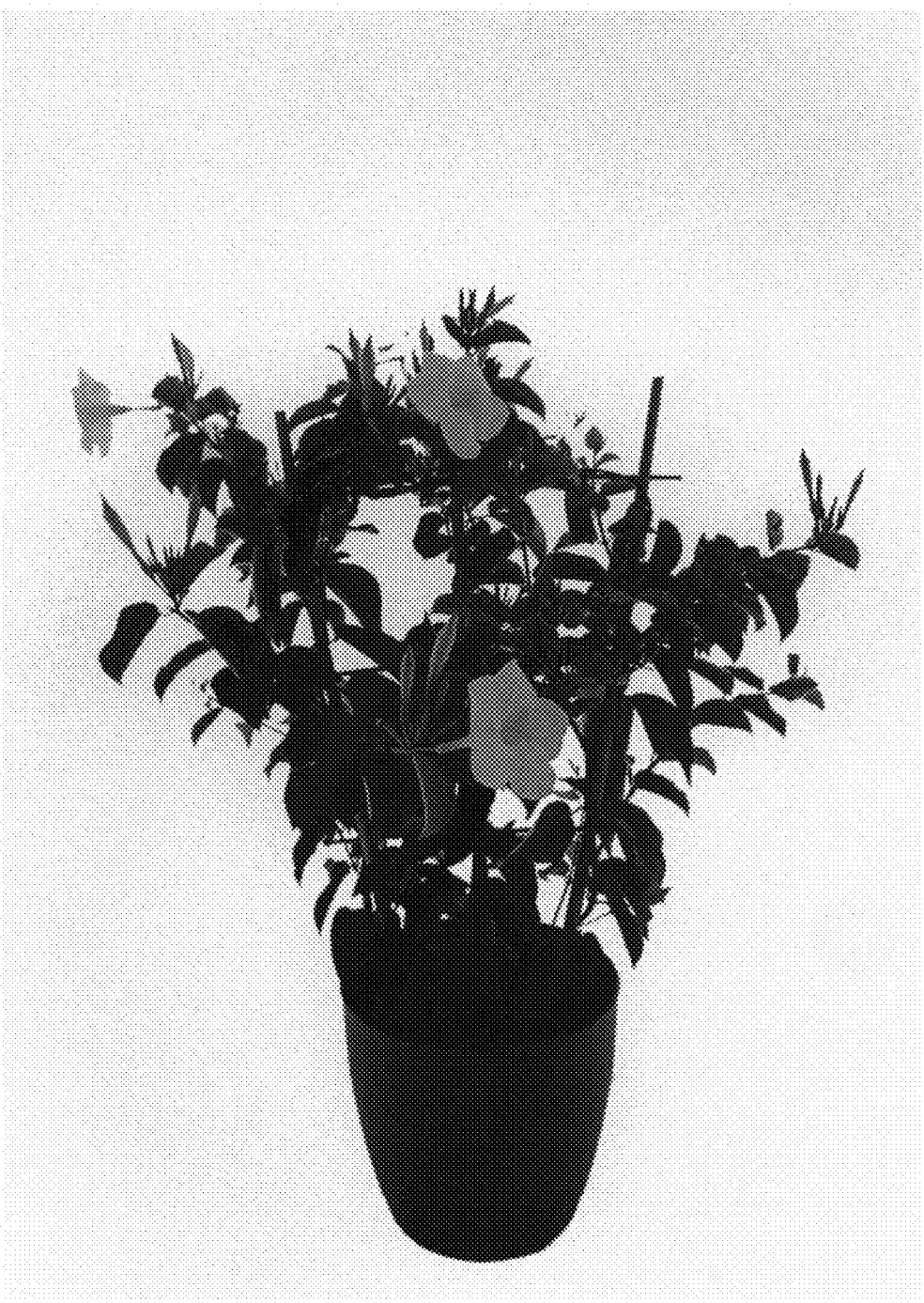

Botanical designation: *Mandevilla sanderi*.
Cultivar denomination: 'LANCONNECTICUT'.

BACKGROUND OF THE INVENTION

The present invention relates to a new and distinct cultivar of *Mandevilla* plant, botanically known as *Mandevilla sanderi* and hereinafter referred to by the name 'Lanconnecticut'.

The new *Mandevilla* plant is a product of a planned breeding program conducted by the Inventor in Motril, Spain. The objective of the breeding program is to create new vigorous and freely branching *Mandevilla* plants with numerous attractive flowers.

The new *Mandevilla* plant originated from a cross-pollination conducted by the Inventor in Motril, Spain in 2016 of a proprietary selection of *Mandevilla sanderi* identified as code number 09-0318-009-EE, not patented, as the female, or seed, parent with a proprietary selection of *Mandevilla sanderi* identified as code number 10-0054-032-EE, not patented, as the male, or pollen, parent. The new *Mandevilla* plant was discovered and selected by the Inventor as a single flowering plant from within the progeny of the stated cross-pollination in a controlled greenhouse environment in Motril, Spain in June, 2017.

Asexual reproduction of the new *Mandevilla* plant by cuttings in a controlled greenhouse environment in Motril, Spain, since October, 2017 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Lanconnecticut'. These characteristics in combination distinguish 'Lanconnecticut' as a new and distinct *Mandevilla* plant:

1. Broadly upright to trailing plant habit.
2. Moderately vigorous growth habit.
3. Freely branching habit.
4. Glossy dark green-colored leaves.
5. Early and freely flowering habit.
6. Bright yellow-colored flowers with yellow orange-colored throats.

Plants of the new *Mandevilla* can be compared to plants of the female parent selection. Plants of the new *Mandevilla* differ primarily from plants of the female parent selection in the following characteristics:

1. Plants of the new *Mandevilla* are more freely branching than plants of the female parent selection.
2. Leaves of plants of the new *Mandevilla* are more pointed than and not as round as leaves of plants of the female parent selection.
3. Plants of the new *Mandevilla* have smaller flowers than plants of the female parent selection.

Plants of the new *Mandevilla* can be compared to plants of the male parent selection. Plants of the new *Mandevilla* differ primarily from plants of the male parent selection in the following characteristics:

1. Plants of the new *Mandevilla* do not require high temperatures for rooting whereas plants of the male parent selection require high temperatures for rooting.

2. Developed flowers of plants of the new *Mandevilla* face outwardly to slightly upright whereas developed flowers of the male parent selection face downward.

Plants of the new *Mandevilla* can also be compared to plants of *Mandevilla sanderi* 'Lancalifornia', disclosed in U.S. Plant Pat. No. 24,074. In side-by-side comparisons, plants of the new *Mandevilla* differ primarily from plants 'Lancalifornia' in the following characteristics:

1. Plants of the new *Mandevilla* are more vigorous than plants of 'Lancalifornia'.
2. Plants of the new *Mandevilla* are more freely branching than plants of 'Lancalifornia'.
3. Plants of the new *Mandevilla* are more freely flowering than plants of 'Lancalifornia'.
4. Plants of the new *Mandevilla* do not require high temperatures for rooting and growth whereas plants of 'Lancalifornia' require high temperatures for rooting and growth.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph on the first sheet (FIG. 1 of 2) comprises a side perspective view of a typical flowering plant of 'Lanconnecticut' grown in a container.

Figure 2:
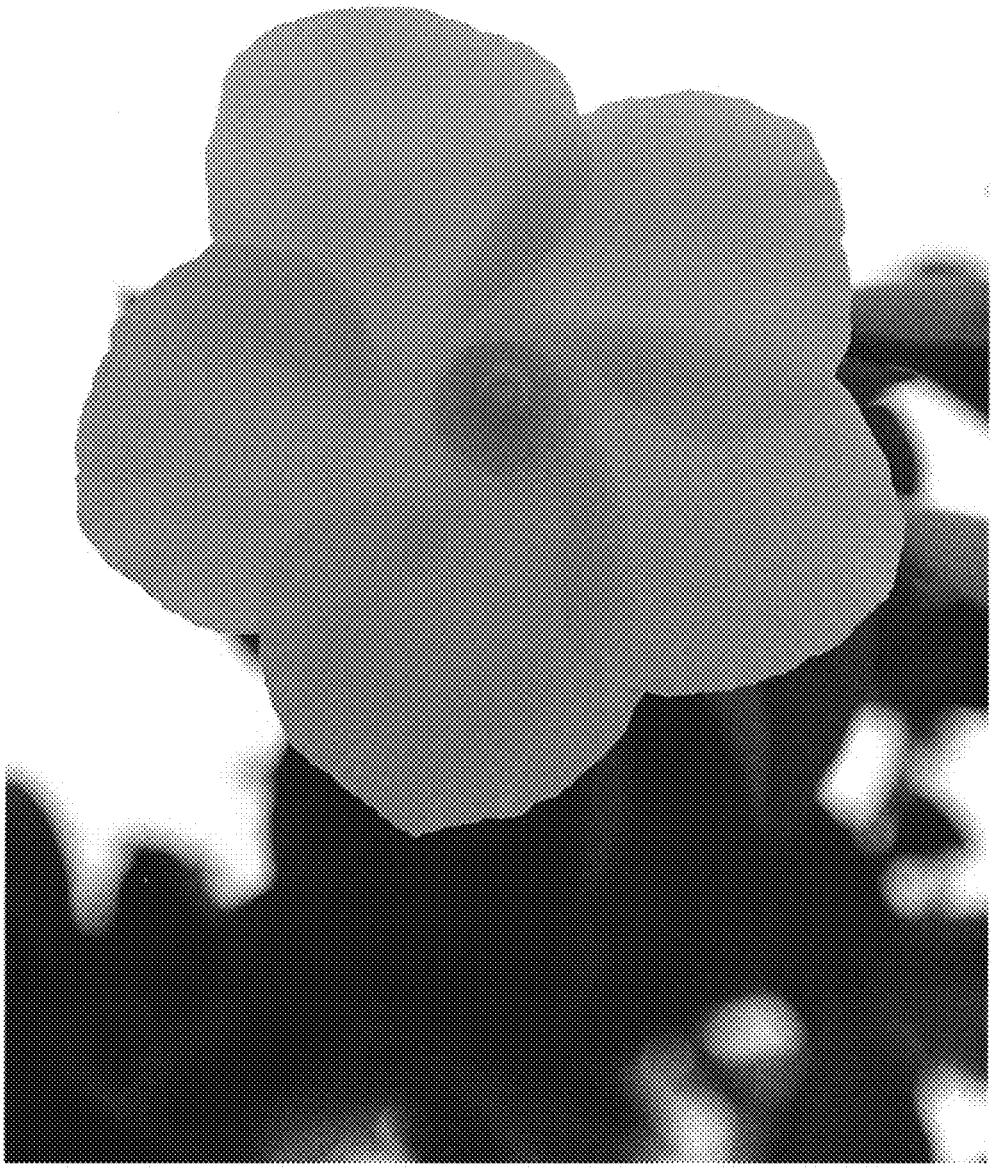

The photograph on the second sheet (FIG. 2 of 2) is a close-up view of a typical open flower of 'Lanconnecticut'.

DETAILED BOTANICAL DESCRIPTION

The aforementioned photographs and following observations, measurements and values describe plants grown during the winter in 15-cm containers in a polyethylene-covered greenhouse in Malause, France and under cultural practices typical of commercial *Mandevilla* production. During the production of the plants, day temperatures ranged from 18° C. to 23° C. and night temperatures ranged from 15° C. to 18° C. Plants were six months old when the photographs and description were taken. In the following description, color references are made to The Royal Horticultural Society Colour Chart, 2015 Edition, except where general terms of ordinary dictionary significance are used.

Botanical classification: *Mandevilla sanderi* 'Lanconnecticut'.

Parentage:

*Female, or seed, parent*.—Proprietary selection of *Mandevilla sanderi* identified as code number 09-0318-009-EE, not patented.

*Male, or pollen, parent*.—Proprietary selection of *Mandevilla sanderi* identified as code number 10-0054-032-EE, not patented.

Propagation:

*Type*.—By vegetative cuttings.

*Time to initiate roots, summer*.—About two weeks at temperatures about 23° C. to 30° C.

*Time to initiate roots, winter*.—About three weeks at temperatures about 18° C. to 25° C.

*Time to produce a rooted young plant, summer*.—About five to six weeks at temperatures about 23° C. to 30° C.

*Time to produce a rooted young plant, winter*.—About eight to ten weeks at temperatures about 18° C. to 25° C.

*Root description*.—Fine, fibrous; typically light yellowish white in color, actual color of the roots is dependent on substrate composition, water quality, fertilizers, substrate temperature and physiological age of roots.

*Rooting habit*.—Freely branching; medium density.

Plant description:

*Plant and growth habit*.—Broadly upright to trailing plant habit; overall plant shape is broadly obovate; moderately vigorous growth habit and moderate to rapid growth rate.

*Plant height, soil level to top of foliar plane*.—About 47.9 cm.

*Plant height, soil level to top of floral plane*.—About 47.9 cm.

*Plant diameter* (*spread*).—About 41.5 cm.

*Lateral branch description*.—Branching habit: Freely branching habit, primary lateral branches with typically eleven secondary lateral branches developing per plant. Length: About 15.1 cm. Diameter: About 3 mm. Internode length: About 2.2 cm. Aspect: Primary lateral branches, mostly erect; secondary lateral branches, about 55° from primary branch axis. Strength: Strong. Texture and luster: Smooth, glabrous; matte; becoming woody with development. Color, developing and developed: Close to 144A to 144B; when woody, close to 199B.

Leaf description:

*Arrangement*.—Opposite, simple.

*Length*.—About 6.3 cm.

*Width*.—About 4.3 cm.

*Shape*.—Ovate, moderately carinate.

*Apex*.—Apiculate to short apiculate.

*Base*.—Cordate to truncate.

*Margin*.—Entire, slightly undulate.

*Texture and luster, upper surface*.—Smooth, glabrous; not rugose; slightly coriaceous; moderately glossy.

*Texture and luster, lower surface*.—Mostly glabrous except for main vein, proximally, pubescent; not rugose; slightly coriaceous; moderately glossy.

*Venation pattern*.—Pinnate.

*Color*.—Developing leaves, upper surface: Close to between 143C and 144A. Developing leaves, lower surface: Close to 146B. Full expanded leaves, upper surface: Close to NN137A; venation, close to 146B. Fully expanded leaves, lower surface: Close to 146A to 146B; venation, close to 145A to 145B.

*Petioles*.—Length: About 7 mm. Diameter: About 1 mm. Strength: Moderately strong. Texture and luster, upper surface: Smooth, glabrous; slightly glossy. Texture and luster, lower surface: Mostly glabrous except for distally, pubescent; slightly glossy. Color, upper surface: Close to 144B. Color, lower surface: Close to 145A.

Flower description:

*Flower type and flowering habit*.—Single salverform flowers arranged singly or in terminal or axillary cymes; flowers rounded star-shaped and face mostly outwardly to slightly upright; freely flowering habit with about 250 flower buds and flowers develop per plant during the flowering season.

*Natural flowering season*.—Plants flower continuously from spring into the autumn in France; plants in full flower about 28 to 30 weeks after planting.

*Flower longevity on the plant*.—About ten days; flowers not persistent.

*Fragrance*.—None detected.

*Inflorescence height*.—About 7 cm.

*Inflorescence diameter*.—About 10.5 cm.

*Flower buds*.—Length: About 5.5 cm. Diameter: About 1 cm. Shape: Narrowly oblanceolate. Texture and luster: Smooth, glabrous; slightly glossy. Color: Distally, close to 153D; proximally, close to 7B; tube, close to 144C.

*Flowers*.—Appearance: Flared trumpet, corolla fused and five-parted. Diameter: About 6.7 cm. Depth (length): About 5.5 cm. Throat diameter: About 1.1 cm. Tube length: About 4.5 cm. Tube diameter: Distally, about 1.3 cm; proximally, about 3.5 mm.

*Petals*.—Quantity and arrangement: Five petals arranged in a single whorl; lower 61.5% portion of the petals are fused into a funnelform tube. Petal length: About 7.3 cm. Petal width: About 3.4 cm. Petal shape and appearance: Unequal spatulate. Petal apex: Obtuse. Petal margin: Entire; moderately and finely undulate. Petal texture and luster, upper surface: Smooth, glabrous; not rugose; moderately velvety; matte. Petal texture and luster, lower surface: Smooth, glabrous; not rugose; slightly velvety; slightly glossy. Throat texture: Smooth, glabrous; moderately velvety. Tube texture: Smooth, glabrous; slightly velvety. Color: Petal, when opening, upper surface: Close to between 12A and 14B. Petal, when opening, lower surface: Close to between 12A and 13B. Petal, fully opened, upper surface: Slightly darker than 12A; venation, slightly darker than 12A; color does not change with development. Petal, fully opened, lower surface: Close to 13B; venation, close to 13B; color does not change with development. Throat: Close to 17A to 17B; proximally, close to 145B; venation, similar to lamina. Tube: Close to 11A; proximally, close to 145A; venation, similar to lamina.

*Sepals*.—Quantity and arrangement: Five sepals arranged in a single whorl. Calyx length: About 1 mm. Calyx diameter: About 3.5 cm. Sepal length: About 1 mm. Sepal width: About 1.2 mm. Sepal shape: Broadly deltoid. Sepal apex: Broadly acuminate. Sepal base: Broadly cuneate. Sepal margin: Entire. Sepal texture and luster, upper and lower surfaces: Smooth, glabrous; slightly glossy. Sepal color: When opening, upper and lower surfaces: Close to 147D; towards the apex, close to 151B. Fully opened, upper and lower surfaces: Close to 147D; towards the apex, close to 151B.

*Peduncles*.—Length: About 1.3 cm. Diameter: About 2.5 mm. Strength: Moderately strong. Aspect: About 35° from vertical. Texture and luster: Smooth, glabrous; matte. Color: Close to 144A.

*Pedicels*.—Length: About 1.8 cm. Diameter: About 2 mm. Strength: Moderately strong. Aspect: About 25° from peduncle axis. Texture and luster: Smooth, glabrous; matte. Color: Close to 144A.

*Reproductive organs*.—Stamens: Quantity and arrangement: Typically five; basifixed; anthers connivent. Filament length: About 1.5 mm. Filament color: Close to 150D. Anther size: About 1.2 mm by 8 mm. Anther shape: Narrowly oblong. Anther color: Close to 158B. Pollen amount: None observed. Pistils: Quantity: Typically one. Pistil length: About 2.3 cm. Style length: About 2.1 cm. Style color: Close to 154C. Stigma diameter: About 2 mm. Stigma shape: Club-shaped, pointed. Stigma color: Lighter than 147D. Ovary color: Close to 144B.

*Seeds and fruits*.—To date, seed and fruit production have not been observed on plants of the new *Mandevilla*.

Pathogen & pest resistance: To date, plants of the new *Mandevilla* have not been noted to be resistant to pathogens and pests common to *Mandevilla* plants.

Temperature tolerance: Plants of the new *Mandevilla* have been observed to tolerate temperatures of about 5° C. to 40° C. and to be suitable for USDA Hardiness Zones 9 through 13.

It is claimed:

1. A new and distinct *Mandevilla* plant named 'Lanconnecticut' as illustrated and described.

* * * * *